United States Patent
Kumke et al.

(10) Patent No.: US 8,022,084 B2
(45) Date of Patent: Sep. 20, 2011

(54) POLYMORPHIC FORMS OF A GABA$_A$ AGONIST

(75) Inventors: Daniel J. Kumke, Rahway, NJ (US); Jerry A. Murry, Rahway, NJ (US); Bryon L. Simmons, Rahway, NJ (US); Feng Xu, Rahway, NJ (US)

(73) Assignee: H. Lundbeck A/S, Valby (DK)

( * ) Notice: Subject to any disclaimer, the term of this patent is extended or adjusted under 35 U.S.C. 154(b) by 332 days.

(21) Appl. No.: 11/813,796

(22) PCT Filed: Jan. 26, 2006

(86) PCT No.: PCT/US2006/002809
§ 371 (c)(1),
(2), (4) Date: Aug. 8, 2007

(87) PCT Pub. No.: WO2006/083682
PCT Pub. Date: Aug. 10, 2006

(65) Prior Publication Data
US 2008/0085913 A1    Apr. 10, 2008

Related U.S. Application Data

(60) Provisional application No. 60/648,151, filed on Jan. 28, 2005.

(51) Int. Cl.
A61K 31/4355    (2006.01)
C07D 498/04    (2006.01)

(52) U.S. Cl. .................................... 514/302; 546/116

(58) Field of Classification Search ................. 546/116; 514/302
See application file for complete search history.

(56) References Cited

U.S. PATENT DOCUMENTS 6,627,646 B2 * 9/2003 Bakale et al. ................. 514/322
2005/0288371 A1 12/2005 Ebert et al.

FOREIGN PATENT DOCUMENTS

| EP | 0000338 | 1/1979 |
| WO | 2004/112786 | 12/2004 |
| WO | 2005/073237 | 8/2005 |
| WO | 2006/053556 | 5/2006 |
| WO | 2006/102093 | 9/2006 |

OTHER PUBLICATIONS

Chemical & Engineering News, Feb. 2003, 32-35.*
Brittain ed., "Polymorphism , etc.," NY: Marcel Dekker, Inc., 1999, 1-2, 183-226.*
US Phamacopia #23, National Formulary #18, 1995, 1843-1844.*
Muzaffar et al., "Polymorphism and Drug, etc.," J of Pharm. (Lahore), 1979, 1(1), 59-66.*
Jain et al., "Polymorphism in Pharmacy". Indian Drugs, 1986, 23(6) 315-329.*
Taday et al., "Using Terahertz, etc.," J. of Pharm. Sci., 2003, 831-838.*
Concise Encyclopedia Chemistry, NY: Walter de Gruyter, 1993, 872-873.*
Doelker, english translation of S.T.P. Pharma Pratiques (1999), 9(5), 399-409, pp. 1-33.*
Doelker, english translation of Ann. Pharm. Fr. 2002, 60: 161-176, pp. 1-39.*
Otsuka et al., "Effect of Polymorphic. etc.," Chem. Pharm. Bull. 47(6) 852-856 (1999).*
Singhal et al., "Drug Polymorphism, etc.," Advanced drug delivery reviews 56, 335-347 (2004).*
CMU Pharmaceuticlal polymorphism, interenet p. 1-3 (2002) (print out Apr. 3, 2008).*
Vippagunta et al., Advanced Drug Deliveryu Reviews 48, 2002, 3-26.*
Mathias et al., "The GABA uptake inhibitor tiagabine promotes slow wave sleep in normal elderly subjects," Neurobiology of Aging, vol. 22, pp. 247-253 (2001).
N'Gouemo et al., "The periaqueductal grey is a critical site in the neuronal network for audiogenic seizures: modulation by GABAA, NMDA and opioid receptors," Epilepsy Research, vol. 35, pp. 39-46 (1999).
Hilfiker, et al., Relevance of Solid State Properties for Pharmaceutical Products, Polymorphism: in the Pharmaceutical Industry, pp. 1-3, (2006).
Hilfiker, et al., Approaches to Polymorphism Screening, Polymorphism: in the Pharmaceutical Industry, Chapter 11, pp. 287-288, (2006).
Bernstein, Polymorphism and Patent from a Chemist's Point of View, Polymorphism: in the Pharmaceutical Industry, Chapter 14, pp. 365-369, (2006).
Florence, et al., Properties of Solid State, Physicochemical Principles of Pharmacy, pp. 21-33, (1988).
Bernstein, Polymorphism in Molecular Crystals, Oxford Science Publications, pp. 9-10, (2002).
European Search Report for counterpart application EP 1018144.8 dated Jan. 14, 2011, 5 pages.
Cara, Mino R., "Crystalline Polymorphism of Organic Compounds" Topics in Current Chemistry, vol. 198, pp. 183-2O8(1998).
Document XP-002610534, Supplementary Technical Information relating to EP06719602, EPOLINE, Apr. 3, 2009 CO7D EPOLINE A61P, A61K3 (Apr. 3. 2009), XP002610534, Retrieved from the Internet: URL:https:// register.epoline.org/espacenet/application?documentId=E0N9AL4T7824FI4 &number=EP06719602&Ing=en&npl=false [retrieved on Nov. 22, 2010].

* cited by examiner

Primary Examiner — Patricia L Morris
(74) Attorney, Agent, or Firm — Fish & Richardson P.C.

(57) ABSTRACT

The present invention is directed to novel polymorphic forms of the compound 4,5,6,7-tetrahydroisoxazolo[5,4-c]pyridin-3-ol hydrate (gaboxadol monohydrate). The invention is further concerned with pharmaceutical compositions containing the polymorphic forms as an active ingredient, methods for treatment of disorders susceptible to amelioration by GABAA receptor agonism with the polymorphic forms, and processes for the preparation of the polymorphic forms.

5 Claims, No Drawings

POLYMORPHIC FORMS OF A GABA$_A$ AGONIST

CROSS REFERENCE TO PRIOR APPLICATIONS

This application is a U.S. national phase of International Application No. PCT/US2006/002809, filed Jan. 26, 2006, which claims priority from U.S. Provisional Application No. 60/648,151, filed Jan. 28, 2005.

BACKGROUND OF THE INVENTION

The compound 4,5,6,7-tetrahydroisoxazolo[5,4-c]pyridin-3-ol (also known as THIP or gaboxadol, and hereinafter referred to as gaboxadol) and is a known GABA$_A$ receptor agonist (see, for example, EP 0 000 338) and has therefore been suggested for use in treating a variety of neurological and psychiatric disorders such as epilepsy, Parkinson's disease, schizophrenia and Huntingdon's chorea. More recently, there has been disclosed the use of gaboxadol for treatment of sleep disorders (WO 97/02813) and premenstrual syndrome (WO 02/40009), and the disclosure that gaboxadol is a particularly potent agonist at GABA$_A$ receptors comprising α4 and δ subunits (Brown et al, British J. Pharmacol., 136, 965-74 (2002).

Other indications for which gaboxadol may be suitable include hearing disorders (especially tinnitus), vestibular disorders, attention deficit hyperactivity disorder, intention tremor and restless leg syndrome.

The preparation of gaboxadol is disclosed in EP 0 000 338, both as the free base and as an acid addition salt (specifically, the hydrobromide), but here is no mention of hydrated forms, and the hydrobromide was the form used for the pharmacological testing described in EP 0 000 338.

Gaboxadol is sold commercially (eg. by Sigma) in the form of the hydrochloride salt, and WO 01/22941 and WO 02/094225 disclose granulated pharmaceutical compositions comprising gaboxadol in the form of the hydrochloride salt.

As detailed in WO 02/094255, use of acid addition salts of gaboxadol such as hydrochloride in the manufacture of pharmaceutical oral dosage forms such as tablets gives rise to corrosion problems when conventional techniques and equipment are employed. There is therefore a need for novel forms of gaboxadol suitable for incorporation in pharmaceutical oral dosage formulations.

Morphological forms of pharmaceutical compounds may be of interest to those involved in the development of a suitable dosage form because if the morphological form is not held constant during clinical and stability studies, the exact dosage used or measured may not be comparable from one lot to the next. Once a pharmaceutical compound is produced, it is important to recognize the morphological form delivered in each dosage form to assure that the production process uses the same form and that the same amount of drug is included in each dosage. Therefore, it is imperative to assure that either a single morphological form or some known combination of morphological forms is present. In addition, certain morphological forms may exhibit enhanced thermodynamic stability and may be more suitable than other morphological forms for inclusion in pharmaceutical formulations. As used herein, a polymorphic form of a chemical compound is the same chemical entity, but in a different crystalline arrangement.

SUMMARY OF THE INVENTION

The present invention is directed to novel polymorphic forms of the compound 4,5,6,7-tetrahydroisoxazolo[5,4-c] pyridin-3-ol hydrate (gaboxadol monohydrate). The invention is further concerned with pharmaceutical compositions containing the polymorphic forms as an active ingredient, methods for treatment of disorders susceptible to amelioration by GABAA receptor agonism with the polymorphic forms, and processes for the preparation of the polymorphic forms.

DETAILED DESCRIPTION OF THE INVENTION

The present invention is directed to polymorphic forms of the compound gaboxadol monohydrate designated as form III and form IV.

Gaboxadol monohydrate polymorphic form III is characterized by characteristic absorption bands obtained from an X-ray powder diffraction pattern at spectral d-spacings of 5.1 and 3.7 angstroms. Gaboxadol monohydrate polymorphic form III is further characterized by spectral d-spacings of 7.5, 3.6, 3.3 and 2.5 angstroms. Gaboxadol monohydrate polymorphic form III is characterized by characteristic absorption bands obtained from an X-ray powder diffraction pattern at spectral d-spacings of 7.5, 5.1, 3.7, 3.6, 3.3 and 2.5 angstroms.

Gaboxadol monohydrate polymorphic form III is further characterized by a solid state $^{13}$C nuclear magnetic resonance spectrum with a peak at 16.9 ppm (with reference to a value of 176.03 ppm for the carbonyl peak of glycine). Gaboxadol monohydrate polymorphic form III is further characterized by a solid state $^{13}$C nuclear magnetic resonance spectrum with peaks at 40.4, 102.3, 103.9, 159.6, 172.6 and 174.0 ppm (with reference to a value of 176.03 ppm for the carbonyl peak of glycine).

Gaboxadol monohydrate polymorphic form IV is characterized by characteristic absorption bands obtained from an X-ray powder diffraction pattern at spectral d-spacings of 4.8 and 3.5 angstroms. Gaboxadol monohydrate polymorphic form IV is further characterized by spectral d-spacings of 7.5, 4.1, 3.6 and 3.1 angstroms. Gaboxadol monohydrate polymorphic form IV is characterized by characteristic absorption bands obtained from an X-ray powder diffraction pattern at spectral d-spacings of 7.5, 4.8, 4.1, 3.6, 3.5, and 3.1 angstroms.

Gaboxadol monohydrate polymorphic form IV is further characterized by a solid state $^{13}$C nuclear magnetic resonance spectrum with a peak at 17.2 ppm (with reference to a value of 176.03 ppm for the carbonyl peak of glycine). Gaboxadol monohydrate polymorphic form IV is further characterized by a solid state $^{13}$C nuclear magnetic resonance spectrum with peaks at 40.4, 102.3, 103.3, 159.5, and 172.8 ppm (with reference to a value of 176.03 ppm for the carbonyl peak of glycine).

Another aspect of the present invention is directed to a process for preparing gaboxadol monohydrate form III comprising the steps of:
(a) dissolving an acid addition salt of gaboxadol in water/isopropanol (35% v:v);
(b) adding sufficient base to provide a pH of about 7;
(c) aging the resulting mixture for the mixture for at least 1 hour at 40° C. and at least 5 hours at ambient temperature; and
(d) collecting gaboxadol monohydrate form III.

Another aspect of the present invention is directed to a process for preparing gaboxadol monohydrate form IV comprising the steps of:
(a) dissolving an acid addition salt of gaboxadol in a solvent selected from:

water/isopropanol (30% v:v); water/acetonitrile (60% v:v); and water/dimethoxyethane (67% v:v);
(b) adding sufficient base to provide a pH of about 7;
(c) aging the resulting mixture for the mixture for at least 2 hours at 40° C.; and
(d) collecting gaboxadol monohydrate form IV.

Another aspect of the present invention is directed to a process for preparing gaboxadol monohydrate form IV comprising the steps of:
(a) dissolving an acid addition salt of gaboxadol in water/acetonitrile (40% v:v);
(b) adding sufficient base to provide a pH of about 7;
(c) aging the resulting mixture for the mixture for at least 3 hours at 40° C.; and
(d) collecting gaboxadol monohydrate form IV.

Another aspect of the present invention is directed to a process for preparing gaboxadol monohydrate form IV comprising the steps of:
(a) dissolving an acid addition salt of gaboxadol in water/n-propanol (30% v:v);
(b) adding sufficient base to provide a pH of about 7;
(c) aging the resulting mixture for the mixture for at least 1 hour at 40° C.; and
(d) collecting gaboxadol monohydrate form IV.

Another aspect of the present invention is directed to a process for preparing gaboxadol monohydrate form II comprising the steps of:
(a) dissolving an acid addition salt of gaboxadol in water;
(b) adding sufficient base to provide a pH of about 6.5;
(c) adding isopropanol to the mixture; and
(d) collecting gaboxadol monohydrate form II.

The above operations for preparing gaboxadol monohydrate form II are typically carried out at ambient temperature. A preferred base is aqueous sodium hydroxide. In step (b), seed crystals of authentic gaboxadol monohydrate of form II are preferably added after about 0.3 to 0.4 equivalents of base have been added. After step (b), the mixture is preferably aged at least one hour. In step (c), preferably at least an equal volume of isopropanol is added slowly. After addition of isopropanol, the mixture is preferably aged at least one hour. The slurry obtained after step (c) may be wet-milled, if desired, to adjust the particle size distribution. In step (d) the product is typically collected by filtration and may be washed (e.g. with aqueous isopropanol) and dried by conventional means.

Gaboxadol monohydrate of form II is characterized by an X-ray powder diffraction spectrum in 2θ values using CuKα radiation having a main peak at 25.20, subsidiary peaks at 14.0, 19.0, 21.6, 24.8, 26.7 and 27.80; d-spacings of 7.6, 6.3, 5.7, 4.7, 4.1 and 3.5 Å; and solid state $^{13}C$ nuclear magnetic resonance spectrum with peaks at 17.5, 40.3, 102.2, 158.5 and 172.5 ppm (with reference to a value of 176.03 ppm for the carbonyl peak of glycine).

A further embodiment of the present invention provides gaboxadol monohydrate drug substance that comprises gaboxadol monohydrate form III or gaboxadol monohydrate form IV present in a detectable amount. By "drug substance" is meant the active pharmaceutical ingredient ("API"). The amount of gaboxadol monohydrate in the drug substance can be quantified by the use of physical methods such as X-ray powder diffraction, solid-state fluorine-19 magic-angle spinning (MAS) nuclear magnetic resonance spectroscopy, solid-state carbon-13 cross-polarization magic-angle spinning (CPMAS) nuclear magnetic resonance spectroscopy, solid state Fourier-transform infrared spectroscopy, or Raman spectroscopy. In a class of this embodiment, about 5% to about 100% by weight of gaboxadol monohydrate form III or gaboxadol monohydrate form IV is present in the drug substance. In a second class of this embodiment, about 10% to about 100% by weight of gaboxadol monohydrate form III or gaboxadol monohydrate form IV is present in the drug substance. In a third class of this embodiment, about 25% to about 100% by weight of gaboxadol monohydrate form III or gaboxadol monohydrate form IV is present in the drug substance. In a fourth class of this embodiment, about 50% to about 100% by weight of gaboxadol monohydrate form III or gaboxadol monohydrate form IV is present in the drug substance. In a fifth class of this embodiment, about 75% to about 100% by weight of gaboxadol monohydrate form III or gaboxadol monohydrate form IV is present in the drug substance. In a sixth class of this embodiment, substantially all of the gaboxadol monohydrate is the gaboxadol monohydrate form III or gaboxadol monohydrate form IV, i.e., the gaboxadol monohydrate drug substance is substantially pure gaboxadol monohydrate form III or gaboxadol monohydrate form IV.

For the avoidance of any doubt, "gaboxadol" as used herein refers to 4,5,6,7-tetrahydroisoxazolo[5,4-c]pyridin-3-ol free base, which is believed to exist as the zwitterion:

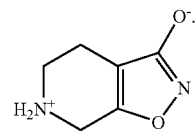

These polymorphic forms of gaboxadol monohydrate are suitable for incorporation in pharmaceutical formulations and may be incorporated in conventional oral dosage formulations such as tablets using conventional techniques and equipment without the risk of corrosion. Furthermore, in view of their significant degree of solubility in water, the novel polymorphs are expected to show bioavailability equivalent to that of the acid addition salts previously used for this purpose. These polymorphic forms have superior properties over other forms of the compound in that it they are more suitable for inclusion in pharmaceutical formulations According to a further aspect of the invention there is provided a pharmaceutical composition comprising, in a pharmaceutically acceptable carrier, gaboxadol monohydrate of form III or form IV, or any combination thereof. Preferably, the composition contains gaboxadol monohydrate of form III or gaboxadol monohydrate of form IV.

The pharmaceutical composition of this invention is a pharmaceutical preparation, for example, in solid, semisolid or liquid form, which contains one or more of the compounds of the present invention as an active ingredient in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea and other carriers suitable for use in manufacturing preparations in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate. Compositions for inhalation or insufflation include suspensions in pharmaceutically acceptable aqueous or organic solvents, or mixtures thereof, and powders. The liquid or solid compositions may contain suitable pharmaceutically acceptable excipients as set out above. Such compositions are administered by the oral or nasal respiratory route for local or systemic effect. Suspension or powder compositions may be administered, preferably orally or nasally, from devices which deliver the formulation in an appropriate manner. The pharmaceutical composition of the invention is preferably in a form suitable for oral administration, such as tablets or capsules. Methods and materials for the formulation of active ingredients as pharmaceutical compositions are well known to those skilled in the art, e.g. from texts such as Remington's Pharmaceutical Sciences (Mack Publishing, 1990).

Gaboxadol monohydrate polymorphs in accordance with the invention is useful in therapeutic treatment of the human body, and in particular the treatment of disorders susceptible to amelioration by GABAA receptor agonism.

Accordingly, the invention further provides a method of treating disorders susceptible to amelioration by GABAA receptor agonism comprising administering to a patient in need thereof a therapeutically effective amount of gaboxadol monohydrate of form III or form IV as defined above.

The invention further provides the use of gaboxadol monohydrate of form III or form IV as defined above, for the manufacture of a medicament for treatment of disorders susceptible to amelioration by GABAA receptor agonism.

In a particular embodiment of the invention, the disorder is susceptible to amelioration by agonism of GABA receptors comprising α4 and δ subunits.

In a further embodiment of the invention, the disorder is selected from neurological or psychiatric disorders such as epilepsy, Parkinson's disease, schizophrenia and Huntington's disease; sleep disorders such as insomnia; premenstrual syndrome; hearing disorders such as tinnitus; vestibular disorders such as Meniere's disease; attention deficit/hyperactivity disorder; intention tremor; and restless leg syndrome.

In a still further embodiment of the invention, the disorder is a sleep disorder, in particular insomnia such as primary insomnia, chronic insomnia or transient insomnia. Within this embodiment is provided the use of the compounds of this invention for the manufacture of a medicament for increasing total sleep time, increasing non-REM (rapid eye movement) sleep time and/or decreasing sleep latency.

The compounds of this invention may be administered to patients in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. A typical dose is in the range from about 5 mg to about 50 mg per adult person per day, e.g. 5 mg, 10 mg, 15 mg, 20 mg or 25 mg daily.

The X-ray powder diffraction spectra was generated on a Philips Analytical X'Pert PRO X-ray Diffraction System with PW3040/60 console. A PW3373/00 ceramic Cu LEF X-ray tube K-Alpha radiation was used as the source. The X-ray powder diffraction spectrum was recorded at ambient temperature (CuKα radiation, 3° to 40° (2θ), steps of 0.014°, 0.2 sec per step), giving the results herein. Solid-state carbon-13 NMR spectrum was obtained on a Bruker DSX 400WB NMR system using a Bruker 4 mm double resonance CPMAS probe. The carbon-13 NMR spectrum utilized proton/carbon-13 cross-polarization magic-angle spinning with variable-amplitude cross polarization. The sample was spun at 15.0 kHz, and a total of 2048 scans were collected with a recycle delay of 20 seconds. A line broadening of 40 Hz was applied to the spectrum before FT was performed. Chemical shifts are reported on the TMS scale using the carbonyl carbon of glycine (176.03 p.p.m.) as a secondary reference.

Example 1

Preparation of Gaboxadol Monohydrate of Form III

Gaboxadol hydrochloride (500 mg) was dissolved in 5 ml water/isopropanol (35% v:v) and was treated with 1 equivalent of 5N NaOH. The solution was stirred for 1 hour at 40° C., then the slurry was aged for 5 hours at ambient temperature (25° C.). The resulting white solid was collected by filtration and air dried to give gaboxadol monohydrate form III.

Example 2

Preparation of Gaboxadol Monohydrate of Form IV

Gaboxadol hydrochloride (500 mg) was dissolved in 5 ml of a solvent selected from: water/isopropanol (30% v:v); water/acetonitrile (60% v:v); or water/dimethoxyethane (67% v:v) and was treated with 1 equivalent of 5N NaOH. The solution was stirred for 2 hour at 40° C. The resulting white solid was collected by filtration and air dried to give gaboxadol monohydrate of form IV.

Gaboxadol hydrochloride (500 mg) was dissolved in 5 ml of water/acetonitrile (40% v:v) and was treated with 1 equivalent of 5N NaOH. The solution was stirred for 3 hour at 40° C. The resulting white solid was collected by filtration and air dried to give gaboxadol monohydrate of form IV.

Gaboxadol hydrochloride (500 mg) was dissolved in 5 ml of water/n-propanol (30% v:v) and was treated with 1 equivalent of 5N NaOH. The solution was stirred for 1 hour at 40° C. The resulting white solid was collected by filtration and air dried to give gaboxadol monohydrate of form IV.

Example 3

Preparation of Gaboxadol Monohydrate of Form II

Gaboxadol hydrochloride (300 g, 1.698 mol) and water (1.2 L) were charged into a 5.0 L resin kettle equipped with temperature control bath, overhead stirrer, $N_2$ inlet, and flow-cell wet mill apparatus at ambient temperature (25° C.). 5N NaOH (102 mL, 0.3 equiv, 0.509 mol) was charged over five minutes at ambient temperature and the solution was aged for 30 min. The batch was seeded with gaboxadol monohydrate form II (15.0 g, 5 wt %). 5N NaOH (238 mL, 1.189 mol) was added over 3 h via a syringe pump while the internal temperature of the vessel was maintained at 25° C. The pH of the reaction slurry is carefully monitored during the base charge with a calibrated pH electrode. When the pH had risen to ~5.5 the syringe motor was turned off and the remaining base (~2 mL) was manually discharged from the syringe dropwise until a pH of 6.5 was obtained. The slurry was further aged for 1 h at ambient temperature. iPrOH (1.86 L) was added dropwise over 2 h at ambient temperature. The slurry was aged with stirring for 1 h. The batch was cooled to an internal temp to 0-10° C. and wet milled at 0-10° C. The slurry was allowed to warm up to ambient temperature (20° C.) and filtered. The wet cake was displacement washed 3×600 mL of 30% water/iPrOH and vacuum/suction dried at 1 atm or reduced pressure under humidity controlled $N_2$ (>15% RH) to give gaboxadol monohydrate form II.

Example 4

Preparation of Gaboxadol Monohydrate of Form II

Gaboxadol hydrobromide (100 g, 0.452 mol) and water (300 mL) were charged into a 2 L vessel equipped with an overhead stirrer, $N_2$ inlet, and additional funnel at ambient temperature (25° C.). 5N NaOH (31 mL, 0.4 equiv, 0.158 mol) was charged over five minutes at ambient temperature and the solution was aged for 30 min. The batch was seeded with gaboxadol monohydrate form II (15.0 g, 5 wt %). 5N NaOH (54 mL) was added over 3 h via a syringe pump while the internal temperature of the vessel was maintained at 25° C. The pH of the reaction slurry is carefully monitored during the base charge with a calibrated pH electrode. The slurry was further aged for 1 h at ambient temperature. iPrOH (450 mL) was added dropwise over 2 h at ambient temperature. The slurry was aged with stirring for 1 h. After wet mill, the slurry was allowed to warm up to ambient temperature (20° C.) and filtered. The wet cake was displacement washed 3×150 mL of 30% water/iPrOH and vacuum/suction dried at 1 atm or reduced pressure under humidity controlled $N_2$ (>15% RH) to give gaboxadol monohydrate form II.

What is claimed is:

1. A compound gaboxadol monohydrate in a polymorphic form which is characterized by characteristic absorption bands obtained from an X-ray powder diffraction pattern at spectral d-spacings of 5.1 and 3.7 angstroms.

2. The compound of claim 1 which is further characterized by characteristic absorption bands obtained from an X-ray powder diffraction pattern at spectral d-spacings of 7.5, 3.6, 3.3 and 2.5 angstroms.

3. The compound of claim 2 which is further characterized by a solid state carbon-13 nuclear magnetic resonance spectrum with a peak at 16.9 ppm with reference to a value of 176.03 ppm for the carbonyl peak of glycine.

4. The compound of claim 3 which is further characterized by a solid state carbon-13 nuclear magnetic resonance spectrum with peaks at 40.4, 102.3, 103.9, 159.6, 172.6 and 174.0 ppm with reference to a value of 176.03 ppm for the carbonyl peak of glycine.

5. A pharmaceutical composition comprising the compound of claim 1 and a pharmaceutically acceptable carrier.

* * * * *